United States Patent
Agon et al.

(10) Patent No.: US 7,681,491 B2
(45) Date of Patent: Mar. 23, 2010

(54) SELF-CLEANING MIXING HEAD FOR PRODUCING A MILK-BASED MIXTURE

(75) Inventors: Fabien Ludovic Agon, Le Bouveret (CH); Christophe S. Boussemart, Lugrin (FR); Alfred Yoakim, St-Legier-La Chiesaz (CH); Antoine Ryser, Lausanne (CH)

(73) Assignee: Nestec S.A., Vevey (CH)

( * ) Notice: Subject to any disclaimer, the term of this patent is extended or adjusted under 35 U.S.C. 154(b) by 330 days.

(21) Appl. No.: 11/743,975

(22) Filed: May 3, 2007

(65) Prior Publication Data

US 2007/0242561 A1    Oct. 18, 2007

Related U.S. Application Data

(63) Continuation of application No. PCT/EP2005/011866, filed on Nov. 7, 2005.

(30) Foreign Application Priority Data

Nov. 11, 2004   (EP) ................................. 04026844

(51) Int. Cl.
*A47J 31/00*    (2006.01)
(52) U.S. Cl. ........................ 99/293; 99/323.1
(58) Field of Classification Search ........... 99/279–323, 99/352–355, 348, 452–459, 485–489, 495, 99/323.1; 366/279
See application file for complete search history.

(56) References Cited

U.S. PATENT DOCUMENTS

| | | | |
|---|---|---|---|
| 2,836,300 A | 5/1958 | Serr ........................... 210/248 |
| 4,715,275 A * | 12/1987 | Getman ........................ 99/494 |
| 5,402,707 A | 4/1995 | Fond et al. .................... 99/295 |
| 5,649,472 A | 7/1997 | Fond et al. .................... 99/295 |
| 5,753,282 A * | 5/1998 | Tortosa ......................... 426/36 |
| 5,762,987 A | 6/1998 | Fond et al. .................. 426/433 |
| 5,826,492 A | 10/1998 | Fond et al. ..................... 99/295 |
| 5,931,080 A | 8/1999 | Roure Boada ............... 99/293 |
| 6,406,730 B1 * | 6/2002 | Banyard et al. .......... 426/330.3 |
| 2003/0232115 A1 | 12/2003 | Eckenhausen et al. ...... 426/477 |
| 2006/0108023 A1 | 5/2006 | Greiwe et al. ............... 141/369 |
| 2007/0031558 A1 | 2/2007 | Lussi ......................... 426/520 |

(Continued)

FOREIGN PATENT DOCUMENTS

CA    2 260 352 A1    7/2000
DE    202 05 626 U1    7/2002

(Continued)

OTHER PUBLICATIONS

European Search Report dated Jul. 1, 2005 from application No. EP 04026844.3.

(Continued)

*Primary Examiner*—Timothy F. Simone
(74) *Attorney, Agent, or Firm*—Winston & Strawn LLP (57) ABSTRACT

A mixing head for producing heated milk in the form of a froth or water-milk mixture. The mixing head includes a steam feed, a milk inlet, a mixing area where the steam feed and milk inlet join and the steam and milk combine, an outlet nozzle for draining the resulting mixture from the mixing head, a rinsing medium supply, a milk supply and a transfer mechanism that provides relative movement between the milk inlet and the rinsing medium supply or the milk supply for selectively bringing the milk inlet into fluid connection with the rinsing medium supply or the milk supply, such that milk or a rinsing medium, as desired, can enter the mixing head at the milk inlet.

22 Claims, 9 Drawing Sheets

FOREIGN PATENT DOCUMENTS

| | | |
|---|---|---|
| DE | 102 39 595 A1 | 3/2004 |
| EP | 0 512 470 A1 | 11/1992 |
| EP | 0 585 607 A1 | 3/1994 |
| EP | 0 604 615 B1 | 7/1994 |
| EP | 0 791 321 A1 | 8/1997 |
| EP | 0 870 457 A1 | 10/1998 |
| EP | 1 374 748 A2 | 1/2004 |
| EP | 1 472 963 A1 | 11/2004 |
| EP | 472 963 A1 | 11/2004 |
| FR | 2 439 042 A | 5/1980 |
| WO | WO 2004/052159 A1 | 6/2004 |

OTHER PUBLICATIONS

International Search Report dated Jun. 19, 2006 from application No. PCT/EP2005/009693.

* cited by examiner

SELF-CLEANING MIXING HEAD FOR PRODUCING A MILK-BASED MIXTURE

CROSS-REFERENCE TO RELATED APPLICATIONS

This application is a continuation of International application PCT/EP2005/011866 filed Nov. 7, 2005, the entire content of which is expressly incorporated herein by reference thereto.

BACKGROUND

The present invention generally relates to the field of producing a milk/water mixture. Such mixture can be prepared for producing a cappuccino-type coffee beverage by adding the mixture on top of a coffee beverage.

A device for producing such a mixture can be a stand-alone solution or integrated into a coffee or other beverage producing machine. As it is known form the prior art, in order to produce such a mixture, water is supplied to a heater unit heating the water and producing steam. The thus generated steam is fed to a mixing head in which, e.g., by applying a Venturi effect, milk supplied from a milk supply and air from an air inlet is sucked into the water steam flow which results in a heated water/milk mixture which can then be drained from an outlet nozzle of the mixing head to a cup.

A well known problem is that after having produced the desired amount of the mixture, the milk inlet of the mixing head, the interior of the mixing head itself as well as the outlet nozzle have been in contact with milk and thus have to be cleaned e.g., by rinsing the milk flow path from the milk inlet to the mixing area and the outlet nozzle. In known devices this is a labor intensive and time consuming process generally requiring a manual rinsing of the milk flow path. The rinsing or cleaning can actually take substantially more time and effort than the step of producing the mixture. The cleaning is particularly difficult when the milk has dried on the surfaces of the mixing head. On the other hand, if the cleaning is not carried out properly and frequently enough, there can be hygienic problems in any subsequent use of the device.

This, there is a need in the art for improved cleaning processes and devices that incorporate the same, and these are now provided by the present invention.

SUMMARY OF THE INVENTION

The present invention now provides a user-friendly cleaning or rinsing process for a mixing head that is used to prepare heated milk-water mixtures. The invention thereby proposes mechanical means and in particular a mechanical arrangement that facilitates the cleaning procedure in order to facilitate the cleaning step and ensure that cleaning is carried out properly.

The invention relates to a mixing head for producing heated milk in the form of a froth or water-milk mixture. The mixing head comprises a steam feed, a milk inlet, a mixing area where the steam feed and milk inlet join and wherein the steam and milk combine to form a mixture, an outlet nozzle for draining the mixture from the mixing head, a rinsing medium supply, and a milk supply. The mixing head further comprises a mechanism for selectively bringing the milk inlet into fluid connection with the rinsing medium supply and the milk supply, such that milk or a rinsing medium can enter the mixing head at the milk inlet.

The mechanism preferably comprises a transfer member that provides relative movement between the milk inlet and the rinsing medium supply or the milk supply. The mixing head may also be designed such that, when the milk inlet is in fluid connection with the rinsing medium supply, any fluid leaving the outlet nozzle is transferred into a milk supply receptacle.

Another embodiment of the invention relates to a mixing head for producing heated milk froth or heated milk/water mixtures comprising a steam feed, a milk inlet, a mixing area where the steam feed and milk inlet join and wherein the steam and milk combine and to form an emulsified mixture, an outlet nozzle for draining the mixture from the mixing head, and a milk supply receptacle. The mixing head also comprises a mechanism for selectively bringing the outlet nozzle into a position in which any fluid leaving the outlet nozzle is transferred actively or passively into the milk supply receptacle.

For this embodiment, a transfer member can be included to provide relative movement between the mixing head and a rinsing medium supply receptacle or a milk supply receptacle.

For either embodiment, the milk inlet can be adapted to be selectively provided in sealing engagement with a milk supply receptacle that includes the milk supply. Also, the steam feed can be a water/steam feed.

Yet another embodiment of the invention relates to a device for producing heated milk comprising a housing and a mixing head comprising a steam feed, a milk inlet, a mixing area where the steam feed and milk inlet join and wherein the steam and milk combine and to form a mixture, and an outlet nozzle for draining the mixture from the mixing head. The device also includes a transfer mechanism for selectively moving the outlet nozzle from a retracted position where the mixing head outlet nozzle are configured and positioned to be cleaned or rinsed, and a product delivery position in which the outlet nozzle protrudes from a front wall of the housing. In the retracted position, the mixing head preferably becomes flush with the front wall of the housing. Also, the mixing head may be displaceable in a rotational movement along at least one guiding curve between the retracted and product delivery positions.

The device may further include a water tank, a pump and a heating unit for producing the steam supplied to the steam inlet of the mixing head. Then the rinsing medium supply receptacle can be selectively put in fluid connection with a circuit connecting a secondary side of the pump with the heating unit.

The invention also relates to a beverage production machine comprising a device or mixing head as disclosed herein.

The invention further relates to a method for cleaning or rinsing of a mixing head for producing heated milk, wherein the mixing device comprises a steam feed, a milk inlet, a mixing area where the steam feed and milk inlet join and wherein the steam and milk combine to form a mixture, an outlet nozzle for draining the mixture from the mixing head, and a milk supply. The method comprises bringing the milk inlet of the mixing head into fluid contact with a rinsing medium supply, and having a rinsing medium from the supply enter the milk inlet and pass through the mixing head to remove milk residues before leaving the mixing head at the outlet nozzle.

In this method, the rinsing medium can be introduced into the milk inlet by the effect of the liquid suction created as a result of passing the steam into the mixing head. Also, the milk inlet can be moved to connect to the rinsing medium supply to the mixing head. This can be achieved by moving milk inlet via a mechanical transfer mechanism. If desired, the mechanical transfer mechanism can be motorized and operatively associated with a control unit that controls the movement of the mechanical transfer mechanism.

BRIEF DESCRIPTION OF THE DRAWINGS

Further advantages, objects and features of the present invention will become evident for the man skilled in the art when reading the following detailed explanation of an embodiment of the present invention taken in conjunction with the figures of the enclosed drawings.

DETAILED DESCRIPTION OF THE PREFERRED EMBODIMENTS

As noted herein, a first aspect of the present invention relates to a device for producing a milk froth or hot milk has a mixing head presenting:

a water steam feed, a milk inlet, the water steam feed and the milk inlet joining in a mixing area of the mixing head, the mixing area being adapted to mix the supplied water steam and milk, an outlet nozzle for draining the mixture from the mixing head, a rinsing medium supply, and a milk supply.

Further on, a mechanism is provided for selectively bringing the milk inlet in a fluid connection with the rinsing medium supply and the milk supply, such that selectively milk or a rinsing medium such as e.g. water can enter the mixing head at the milk inlet.

The mixing head can be designed such that, when the milk inlet is in fluid connection with the rinsing medium supply, any fluid leaving the outlet nozzle is transferred into a milk supply receptacle.

According to another aspect of the present invention, a device for producing a mixture of milk and water steam has means for selectively bringing the outlet nozzle in a position in which any fluid leaving the outlet nozzle is transferred into a collecting receptacle, which can be e.g., the milk supply receptacle or a separate waste tank.

The milk inlet of the mixing head can be adapted to be selectively in a sealing engagement with a milk supply receptacle for containing the milk supply. Transfer means can be provided for a relative movement of the mixing head and a rinsing medium supply receptacle, or transfer means can be provided for a relative movement of the mixing head and a milk supply receptacle.

According to a still further aspect of the present invention a device for producing a mixture of milk and water steam has a mechanism for selectively moving the outlet nozzle inside and outside a front wall of the casing. The mixing head can be displaceable along a guiding curve. The advantage thereof lies in the simplification of the device by using only one motor to drive the mixing head in motion along a combination of vertical and horizontal directions.

The rinsing medium supply receptacle can be selectively put in fluid connection with the water source, in particular, with the main water delivery line downstream of the water pump. A valve is provided to control the filling of the rinsing medium receptacle with water as the rinsing medium.

A still further aspect of the present invention relates to a beverage production machine comprising such a device for producing a mixture of milk and water steam.

The invention also proposes a method for cleaning or rinsing a mixing head of a device for producing a milk froth or hot milk using water steam, the method comprising the following steps:

bringing a milk inlet of the mixing head in fluid contact with a rinsing medium supply, and having the rinsing medium enter the milk inlet and pass through the mixing head and to leave the mixing head at the outlet nozzle.

The method also comprises entering the rinsing medium in the milk inlet by effect of the liquid suction created as a result of passing water steam in the mixing head. In other words, one takes advantage of the suction effect created normally to draw the milk in the device in order to rinse the device by the rinsing medium that replaces the milk in the rinsing process.

More particularly, the effect of liquid suction is obtained by a Venturi means placed in the mixing head.

Figure 1:
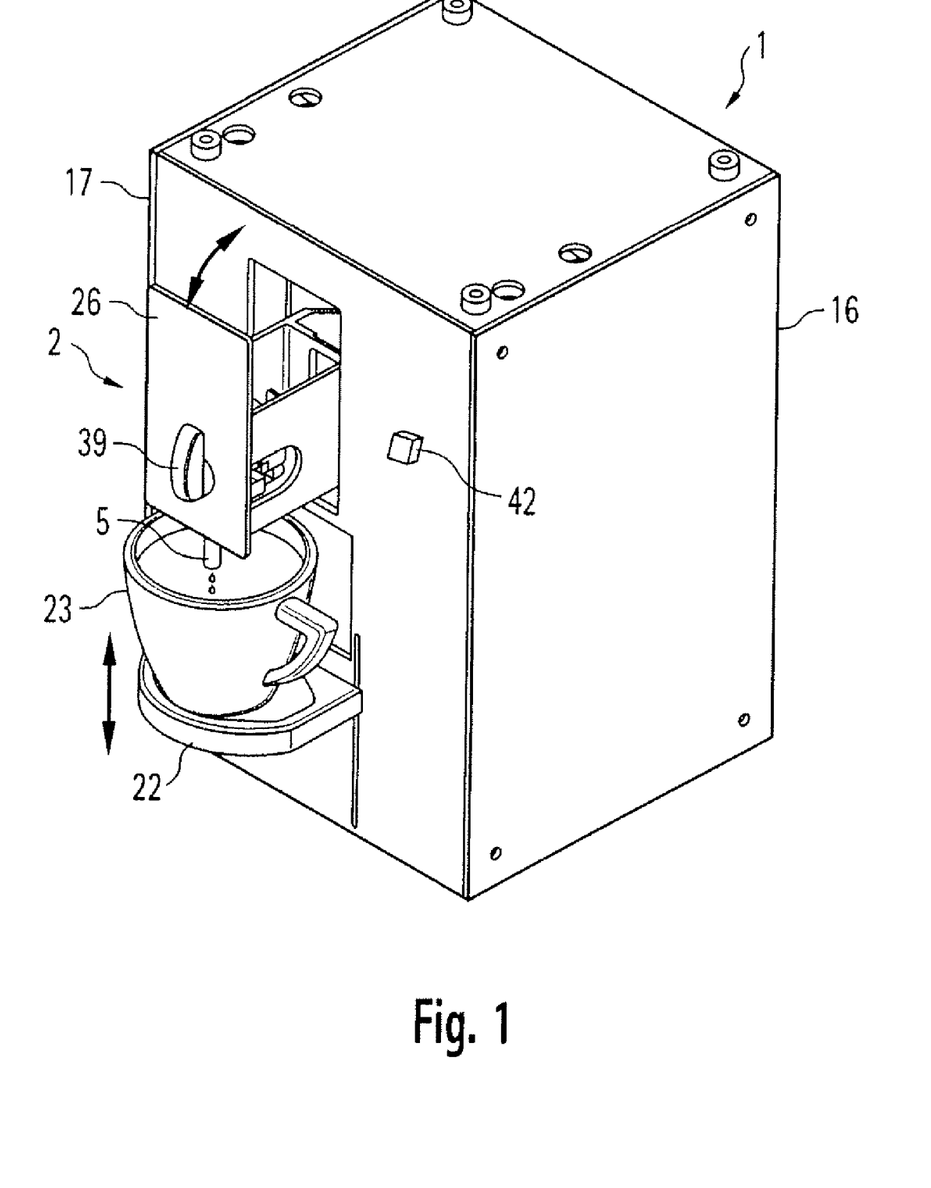
FIG. 1 shows a first perspective view of a device according to the present invention.

FIG. 1 shows the outer appearance of a milk/water mixture production device 1. Such a device 1 can be a stand-alone solution as shown in FIG. 1, but can also be integrated in a coffee machine or other beverage production devices.

The device 1 comprises a casing 16 having a front wall 17 directed towards a user. On the front wall 17 of the casing 16 a mixing head 2 is provided, which can be moved at least in a plane perpendicular to the front wall 17 of the casing 16.

Alternatively or additionally also a displacement of the mixing head in a plane parallel to the front wall of the casing can be envisaged.

Particularly the mixing head 2 can at least assume a first operation position as shown in FIG. 1 in which the mixing head protrudes from the front wall 17 of the housing 16. As will be explained later on, in another position the mixing head can be retracted such the front plate 26 of the mixing head 2 becomes essentially flush with the front wall 17 of the housing 16.

Preferably the mixing head 2 can not only assume different horizontally displaced positions, but also vertically displaced positions.

From an outlet nozzle 5 of the mixing head 2 the produced water/milk mixture can be drained in order to supply it to a receptacle such as e.g. a coffee cup 23 provided on a height-adjustable support 22. In case in the cup 23 a coffee beverage is already present before the water/milk mixture eventually having a foamy texture is introduced, a cappuccino-style beverage can be produced.

The mixing head 2 presents a control button 41 upon activation of which different operating modes of the device 1 can be triggered by a user. The device 1 is programmed to assume the subsequent one a cyclic sequence of operating modes upon activation of the control button 41. The different operating modes will be explained later on with reference to FIGS. 6, 7, and 8. The control button or any alternative or additional user interface can also be provided at other parts of the device 1.

Figure 2:
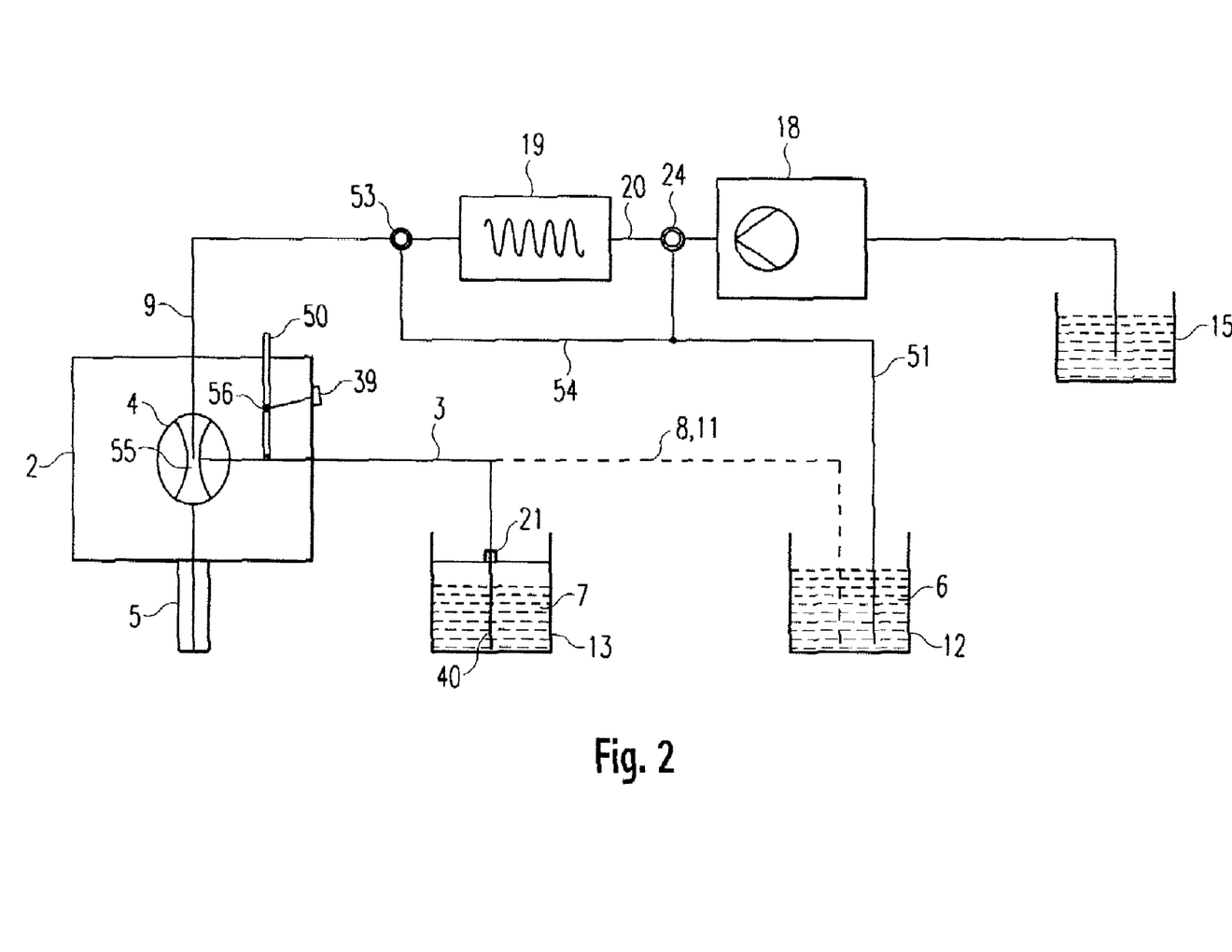
FIG. 2 is a schematic block diagram showing the media streams in a device according to the present invention.

FIG. 2 shows a schematic flow chart of the media streams in such a device 1.

As it is known from prior art devices, water from a water supply 15 (water tank or water conduit) is pumped to a heating block 19 by a pump 18. The heating block 19 produces water steam on demand, which water steam is then fed to the mixing head 2 via a water steam inlet 9.

As shown in FIG. 2 the mixing head 2 comprises a mixing area 4 in which the supplied water steam from the water steam inlet 9 is mixed with a second medium, such as for example milk from a milk inlet 3. The mixing head 4 comprises a Venturi effect zone 55 with reduced cross-section configured to create a local acceleration of the water steam therethrough. As water steam is accelerated in the zone with reduced cross-section, this creates a lowered static pressure at the intersection between the water steam and milk inlets. As a result of this lowered static pressure, milk is sucked into the mixing head 2. In order to produce the froth, air must also be drawn into the mixing area, as a result of the Venturi effect. To this regard an air inlet 50 is provided, for instance, at the intersection with the milk inlet (as shown) or alternatively, directly at the intersection with the mixing area. The control switch 39 manipulates a valve 56 for regulating the amount of air which can be sucked in through the air inlet 50.

Having a pressurized water steam flow through the mixing area 4, milk from the milk inlet 3 is sucked in and a foamy water steam/milk mixture can thus be produced due to the turbulence in the mixing area 4. Such water/milk mixture can then be drained from the outlet nozzle 5 of the mixing head 2.

The control switch 39 can be provided to regulate the ratio milk:air in the mixing head by acting on the air inlet valve 56. In one possible position of the switch 39 and the valve 56, air delivery can even be totally suppressed for delivering hot milk only. In other incremental positions, the ratio milk:air can be varied to vary the volume of froth.

As it is also known from the prior art, the milk inlet 3 of the mixing head 2 can be in fluid connection with milk 7 contained in a milk receptacle 13, which milk receptacle can be provided in the interior or at the exterior of the casing 16 of the device 1. Only as a matter of illustration in the following an example will be explained in which the milk receptacle 13 for the milk supply 7 is housed inside the housing 16 of the device 1.

In order to assist to the Venturi effect and to ensure a proper connection with the milk source, the milk inlet 3 is connected to the milk receptacle 13 by means of a sealing connector 21. The sealing connector 21 presents a resilient (e.g. rubber-elastic) upper contact surface having an opening into which the lower end of the milk inlet 3 penetrates in order to produce a sealed connection.

The sealing connector 21 is in tight fluid connection with a pipe 40 which extends almost to the bottom of the milk receptacle 13 to ensure that essentially all of the milk supply 7 can be sucked in.

According to the present invention it is proposed that the milk inlet 3 of the mixing head 2 can not only be brought in fluid connection with the milk supply 7 in the milk receptacle 13, but also with a second (rinsing) medium such as, for example, water 6 contained in a second receptacle 12, which is physically separated from the milk receptacle 13. Generally in the second receptacle 12 a rinsing medium such as for example water 6 or an other cleaning or rinsing food-compatible media can be supplied.

To provide for the selective fluid connection of the milk inlet 3 to the first receptacle 13 and the second receptacle 12, respectively, a manual or automatic transfer mechanism 8, 11 is provided for a relative movement between the milk inlet 3 and the two receptacles 12, 13.

Again, although in the following description it will be explained how the milk inlet 3 and actually the entire mixing head 2 is transferred to several different positions, it is obvious that alternatively or additionally the position of at least one of the receptacles 12, 13 can be changed by a manual or automatic transfer mechanism for providing the selected fluid connection of the milk inlet 3.

Water as a rinsing medium can e.g. be fed from a valve 24 at the downstream side of the pump 18 to the receptacle 12 through a rinsing fluid filling conduit 51.

After having produced water steam, a certain over-pressure will still be present at the downstream-side of the heating block 19. Such excess water steam can be released to the rinsing medium receptacle 12 by means of a purging valve 53 and a purging conduit 54.

Figure 3:
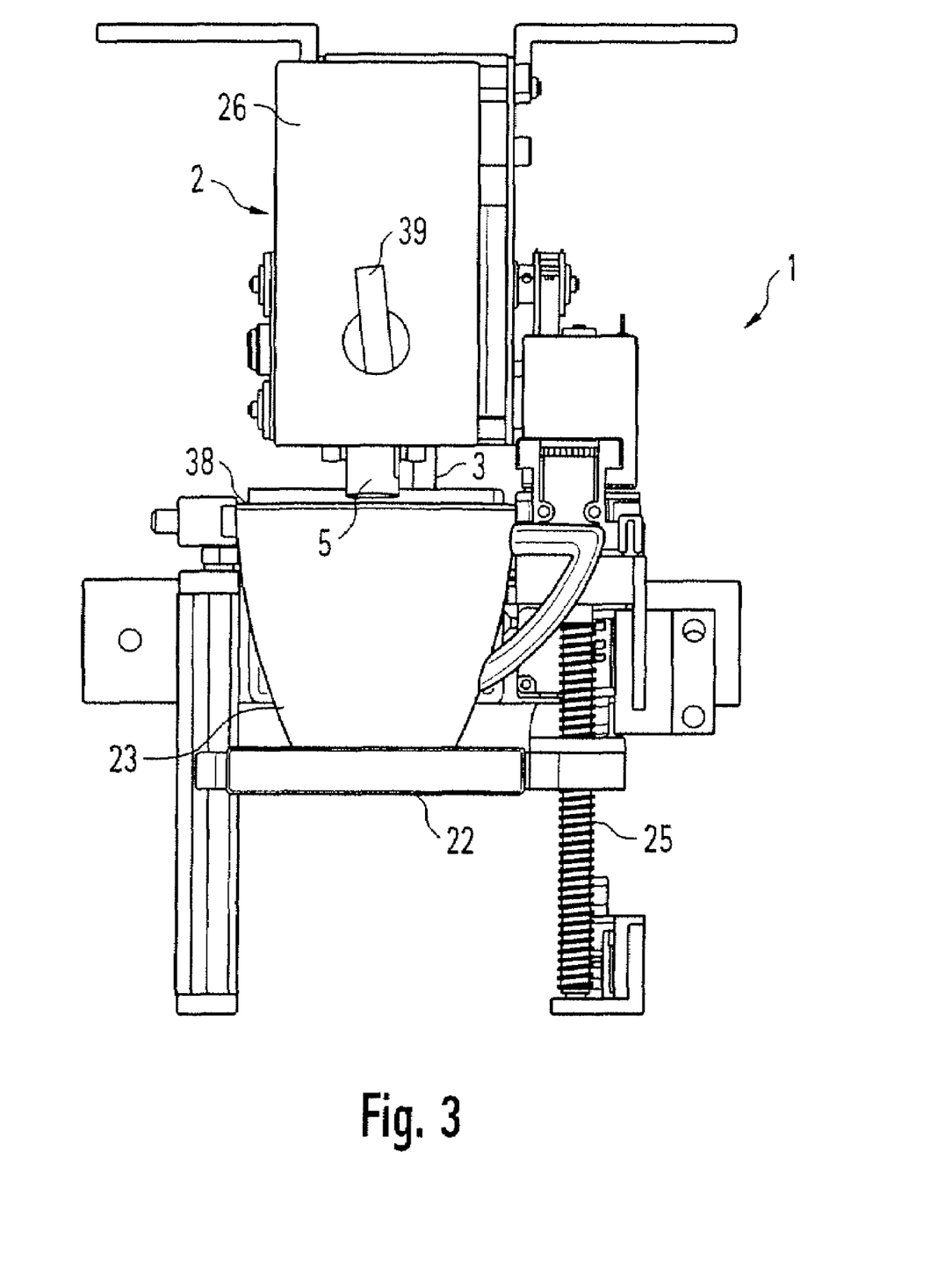
FIG. 3 shows a front view without the housing of the device.

FIG. 3 shows a front view of a device 1 according to the present invention, wherein in this view as well as the following views according to FIG. 4 to 8 the housing 16 is omitted for a better illustration of the relevant parts in the interior of said housing 16.

As can be seen from FIG. 3, the support 22 for the coffee cup 23 is height-adjustable for example by means of a manually operated or motor-driven spindle 25.

Particularly, it can be foreseen that an optical or mechanical sensor detects the upper rim 38 of the cup 23 to ensure a constant level of such rim 38 of the cup 23 vis-à-vis the outlet nozzle 5 of the mixing head 2 independently from the size of the cup 23. In other words, controlled by the sensor the spindle 25 can be operated manually or automatically such that the height of the support 22 for the cup 23 is adjusted such that in turn the upper rim 38 has the desired vertical distance to the lower edge of the outlet nozzle 5 of the mixing head 2. In the illustrated example, a mechanical position sensor 52 in the form of an hinged horizontal plate is positioned to engage the upper rim 38 of the cup 23. When the rim 38 contacts the plate, a signal is sent to the control unit (see FIG. 9). Depending on the location of the sensor, the control device may further control a predetermined downward motion of the cup support along the spindle to properly position the cup in its final delivery position at the proper distance from the outlet nozzle 5.

As can also be seen from FIG. 3, the milk inlet 3 is horizontally offset vis-à-vis the outlet nozzle 5.

Figure 4:
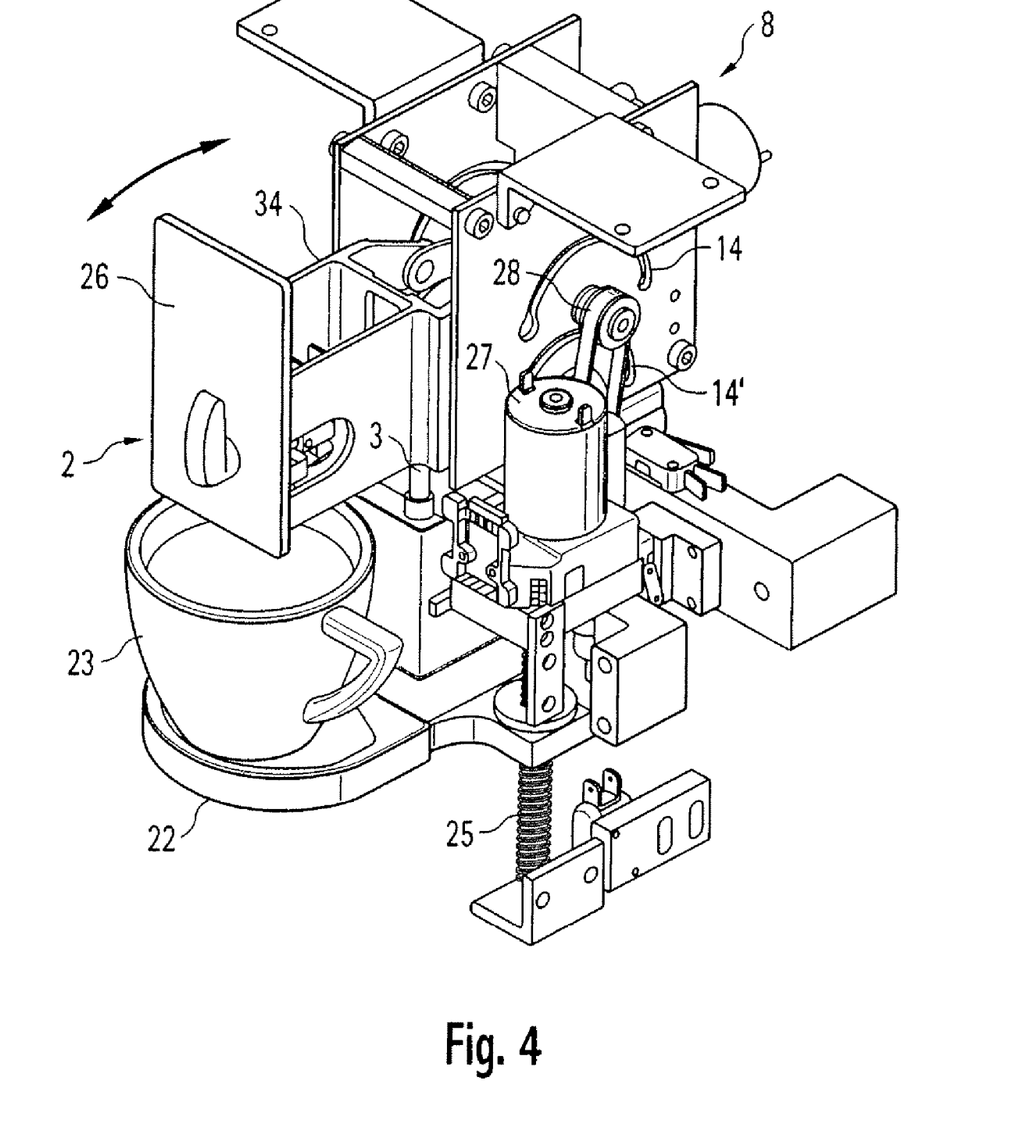
FIG. 4 shows a perspective view without the housing.

As can be seen from FIG. 4, the mixing head 2 having a front cover plate 26 is actually supported by a supporting structure 34. The supporting structure 34 connects the mixing head 2 to a transfer mechanism which is generally referenced with the numeral 8 in FIG. 4. The transfer mechanism 8 can comprise an electric motor 27, a belt drive 28 and guiding curves 14, 14'. Via the guiding curves 14, 14' and operated by the motor 27 and the belt drive 28 the support structure 34 and thus the mixing head 2 can carry out a transfer movement which essentially follows the trajectory of the guiding curves 14, 14'.

By having two essentially parallel guiding curves 14, 14' it can be assured that the mixing head 2 carries out the corresponding translational movements without having its position rotated. Correspondingly, the vertical front plate 26 of the mixing head 2 will always maintain its vertical position independently from the vertical or horizontal position of the mixing head 2.

Other designs are possible according to which the mixing head alternatively or additionally carries out a rotational displacement.

Note that the present invention also encompasses manually driven transfer mechanisms as long as they can assure a relative movement between at least the milk inlet 3 of the mixing head 2 and two physically separated receptacles.

It is to be mentioned that for example by means of such an electric motor alternatively or additionally at least one of the two receptacles 12, 13 could be displaced selectively.

Due to the design of the guiding curves 14, 14' as shown in FIG. 4 the mixing head 2 will carry out a combined movement having both horizontal and vertical components. In other words, guided by the guiding curves 14, 14' the mixing head will both change its horizontal position as well as its vertical position. For example as shown in FIG. 1 the mixing head 2 can be moved into a protruding position in which the mixing head and especially the front cover 26 of the mixing head 2 protrudes from the front wall 17 of the casing 16 of the device 1.

Note that different kinematics for the mixing head 2 can be provided having even more complex movements or having simplified movements, i.e. only vertical or horizontal components and any combination thereof.

Figure 5:
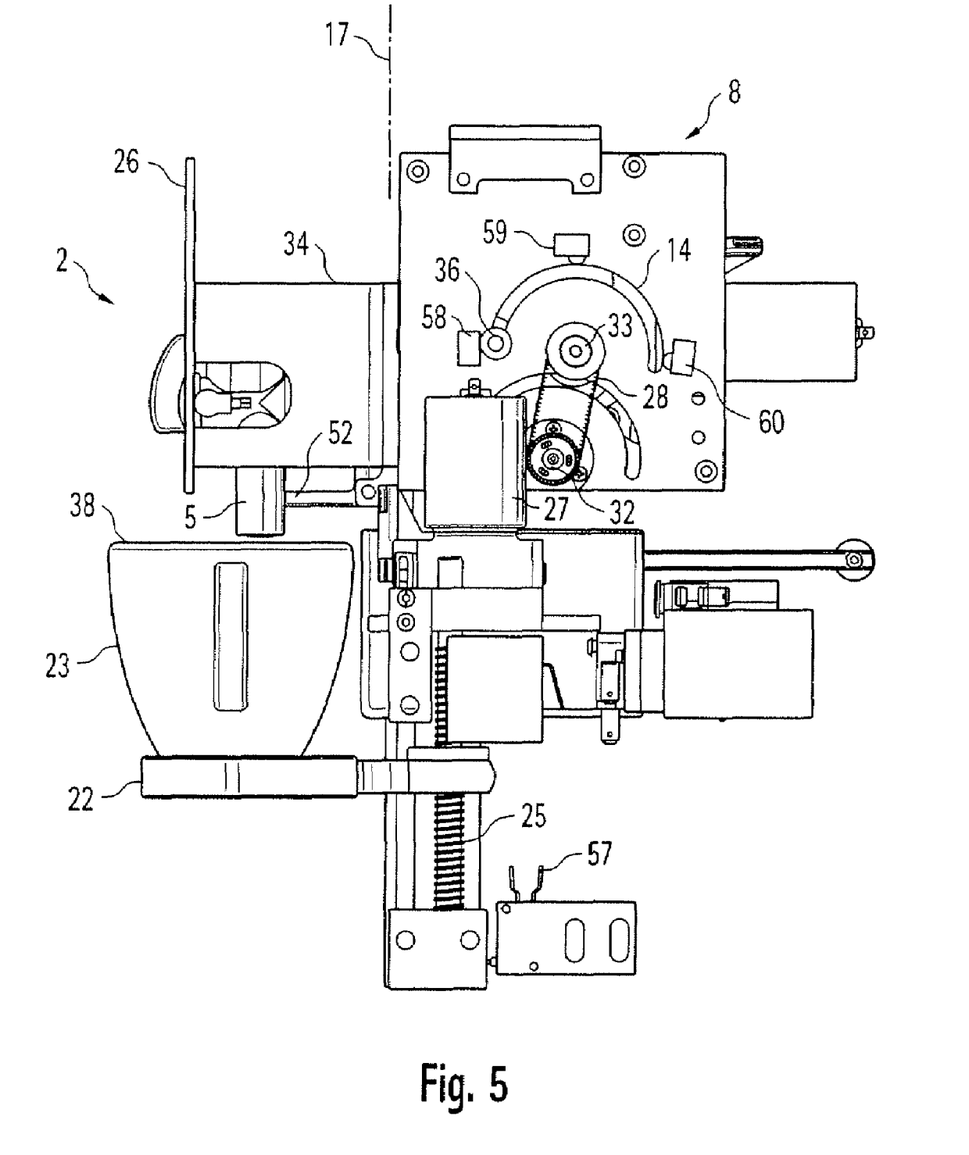
FIG. 5 shows a side view without the housing.

FIG. 5 shows more details of the transfer mechanism 8. The electric motor 27 moves a first pulley 32 in order to move a belt 28, which in turn moves a second pulley 33.

In FIG. 5 also the position sensor 57 for detecting the lower position of the spindle drive and the support 22 as well as the mechanical detector 52 for the upper rim 38 of the cup 23 can be seen.

Figure 6:
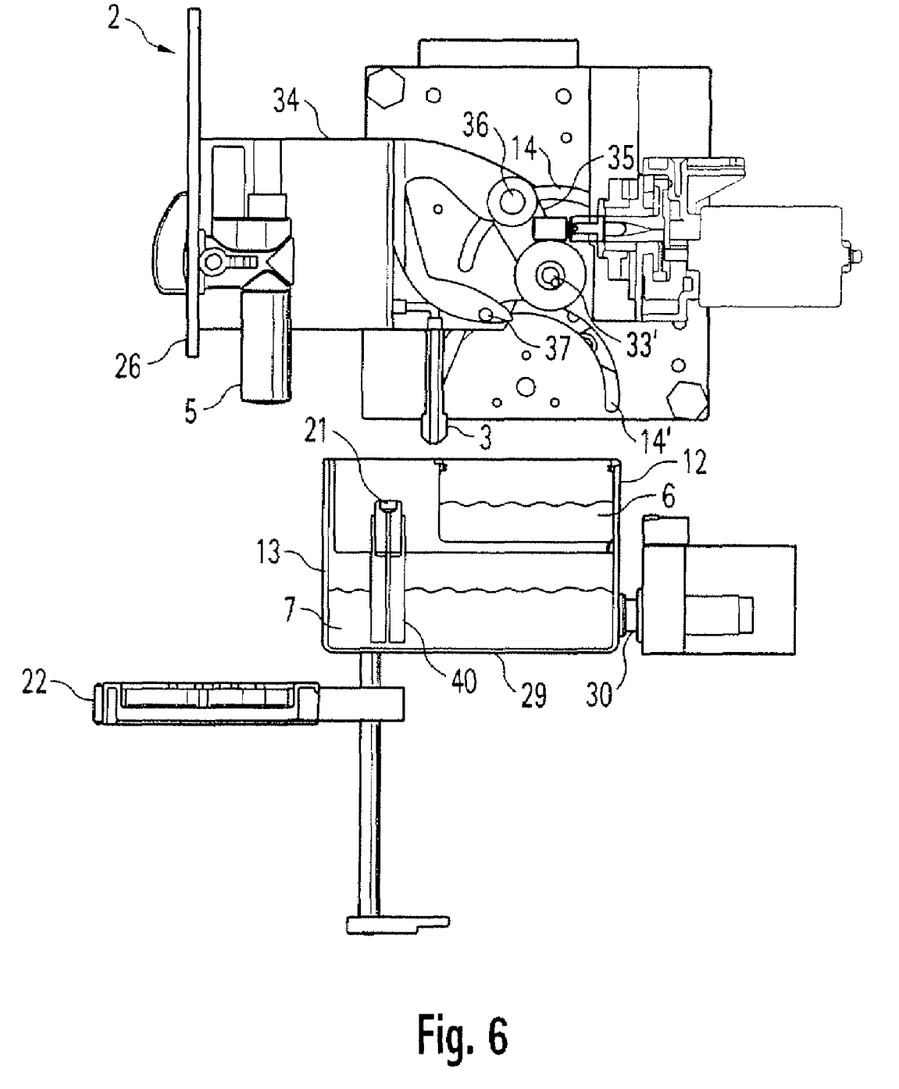
FIG. 6 shows the device in an intermediate position in which the milk receptacle can be inserted into or removed from the device.
Figure 9:
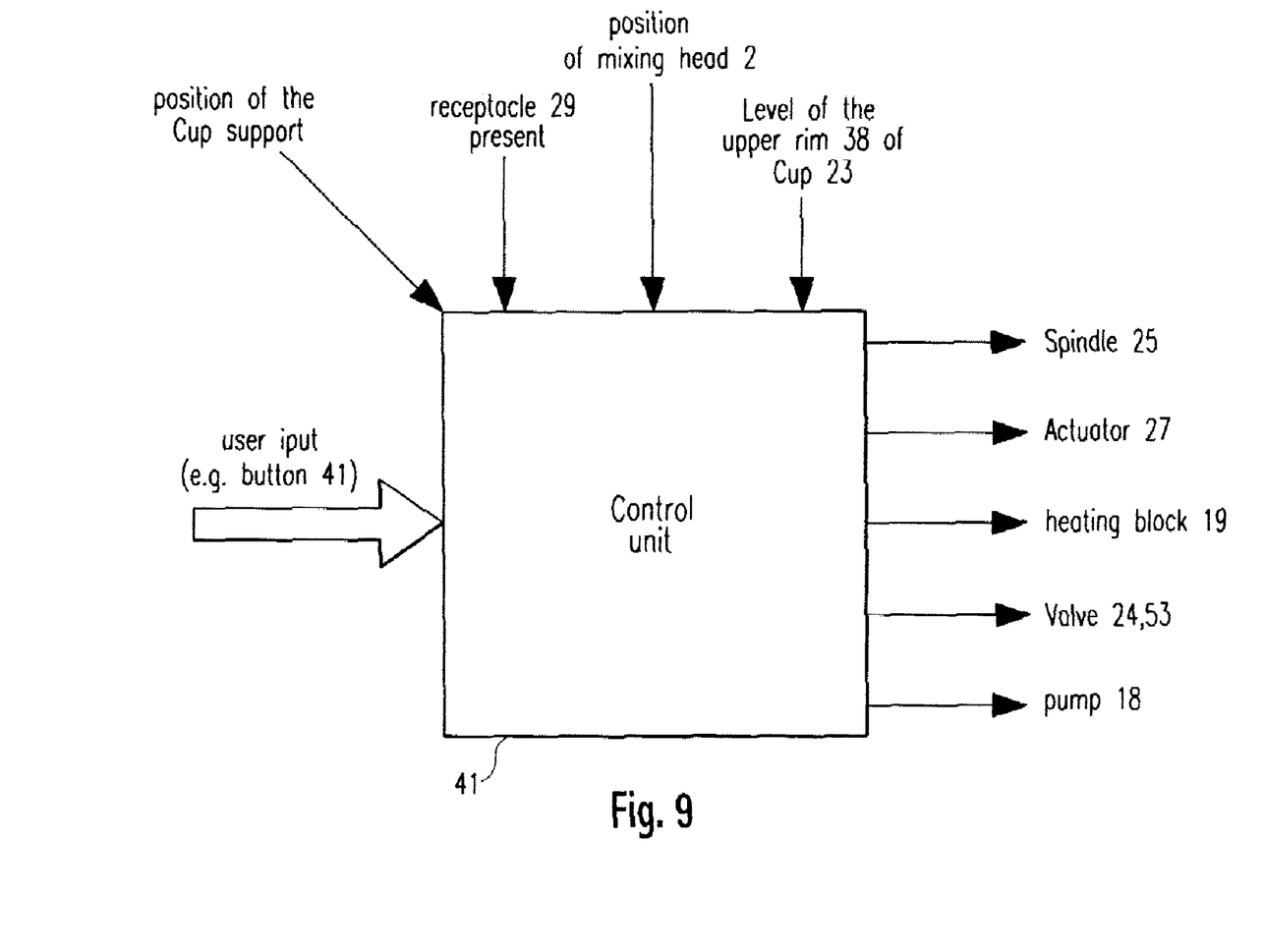
FIG. 9 shows schematically a control unit according to the present invention.

Finally, in order to detect the current state of the mixing head, at the guiding curve 14 the following contact switches respectively operated by a cam 36 are provided:

a contact switch 58 for detecting the position of the mixing head 2 corresponding to the operating mode shown in FIG. 5, a contact switch 59 for detecting the position of the mixing head 2 corresponding to the stand-by mode shown in FIG. 6, and a contact switch 60 for detecting the position of the mixing head 2 corresponding to the stand-by mode shown in FIG. 9.

As can be seen from FIG. 6 showing the opposite side of the device in a state corresponding to FIG. 5, the secondary side pulley 33 is connected to a lever actuator 35 by means of a rotating belt 33'. The actuator lever 35 is connected to the support structure 34 of the mixing head 2 by means of a cam 36 which can be moved forth and back (operated by the belt drive 8 and the electric motor 27) inside the guiding curve 14.

A second cam 37 is provided to follow passively the movements of the first cam 36 in the second guided curve 14'. The second cam assures the constant orientation of the mixing head 2 during the course of the translational displacements.

From FIG. 6 it can be seen that inside the housing 16 a combined receptacle 29 is provided having the already mentioned milk supply 7 in a milk supply receptacle 13 as well as a rinsing medium supply 6 and a second receptacle 12.

The combined receptacle 29 can be inserted and removed, respectively, from the casing 16. To verify the presence of such combined receptacle 29 inside the housing 16 a contact switch 30 is provided.

FIG. 6 shows the device in an intermediate state in which the mixing head 2 is in a lifted position in the middle of the guiding curves 14, 14' such that the combined receptacle 29 can be removed or inserted from/into the housing 16 with ease. The receptacle can then be removed by the user for emptying the receptacle from the rinsing medium and for proper cleaning of the receptacle e.g. in a dishwashing machine.

In order to assume such position a non-shown control device controls the electric motor 27 such that the mixing head 2 and the support structure 34 assume the position as shown in FIG. 6.

Furthermore, in each position taken by the head, switches are provided to sense the position of the transfer mechanism 8, for instance, of the cam with respect to the static part of the mechanism, so that the motor 27 is stopped by the control device when the proper position has been sensed by the proper switch and a corresponding signal has been sent to the control device.

In such a position of the mixing head 2 a user can insert a combined receptacle 29 containing both milk 7 in the receptacle 13 as well as a rinsing medium such as water 6 in the second receptacle 12. After having inserted the combined receptacle 29 inside the housing 16 of the device 1 the user can then position a coffee cup 23 on the support 22.

Figure 7:
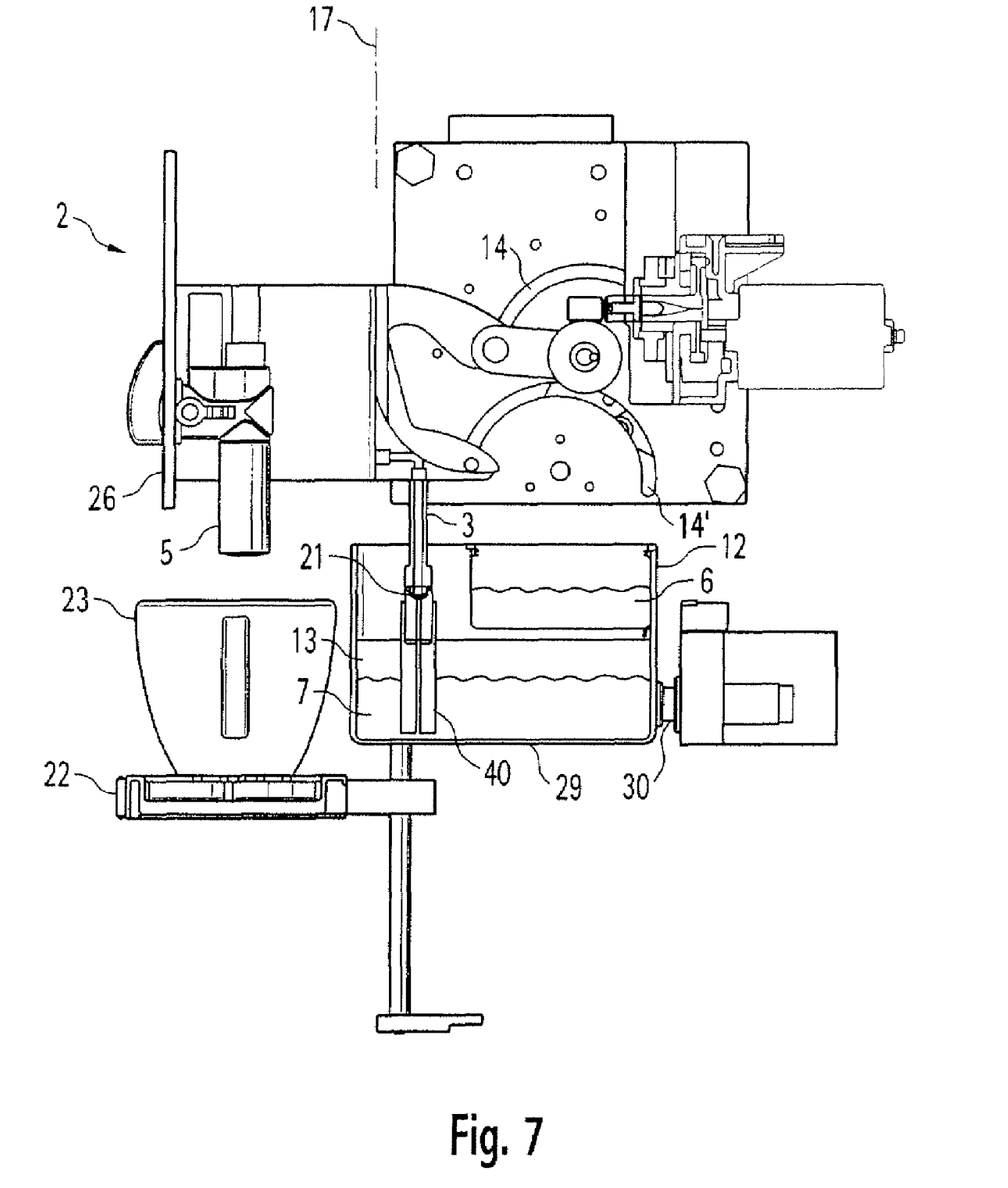
FIG. 7 shows the device in an operating position in which a produced mixture can be drained from the mixing head.

Automatically or triggered by a user input the control of the device 1 can then transfer the support 34 and the mixing head 2 on the position shown in FIG. 6 (intermediate position) into the operation position as shown in FIG. 7. In the position as shown in FIG. 7 the mixing head 2 is lowered again and has assumed a first end position vis-à-vis the guiding curves 14, 14'. Such position can be described as the maximum protruding and lowered position. This position according to FIG. 7 corresponds to the view as shown in FIG. 1. Again, in a fully automatic scheme of control, each position; i.e., the protruding position and the lowered position, will be sensed by a corresponding switch (not shown) and a corresponding signal sent to the control device for stopping the motor 27.

In such a position as depicted in FIG. 7 the milk inlet 3 will be in a sealed connection (connected 21) with the milk supply 7 provided in the milk receptacle 13. In such a state water steam can be fed to the mixing area 4 of the mixing head 2 (please see FIG. 1) and milk from the milk receptacle 13 will be sucked in due to the Venturi effect, such that finally a water/milk mixture eventually with a foamy texture will be drained from the outlet nozzle 5 of the mixing head 2. In such an operation of the mixing head 2 the milk head from the connecting end of the milk inlet 3 to the mixing area and the outlet nozzle 5 of the mixing head 2 will be contaminated with milk, which will eventually dry after the use and which will constitute an undesired growth medium for any micro organisms.

Figure 8:
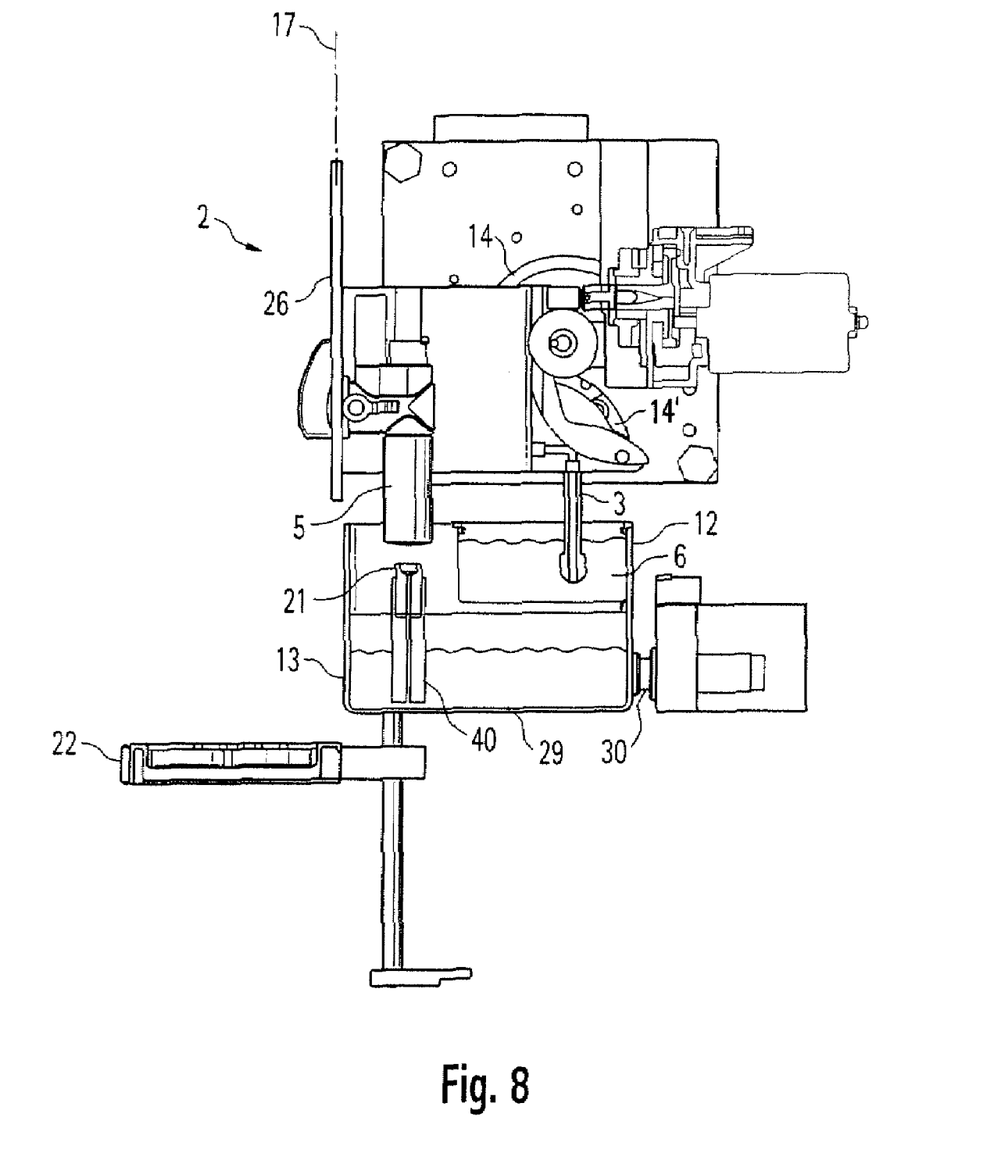
FIG. 8 shows the device in a retracted rinsing position.

Therefore, according to the present invention, the mixing head will, upon completion of the mixture production, automatically or manually be transferred from the position as shown in FIG. 7 to the position as shown in FIG. 8. In the position as shown in FIG. 8 the support structure 34 of the mixing head 2 is in the rearward end position of the guiding curves 14, 14'.

In such a position the front plate 26 flushes with the front wall 17 of the housing 16, which is schematically depicted in FIG. 8.

In such a position the milk inlet 3 of the mixing head 2 is in fluid connection with the rinsing medium 6 contained in the second receptacle 12. As soon as such a position is detected by contact switches (not shown in FIG. 8), the control of the device 1 will again pump water through the heating block 19 and into the mixing area 4 of the mixing head 2. However, as the milk inlet 3 is now in fluid connection with a rinsing medium 6 contained in the second receptacle 12, not milk but a rinsing medium will be sucked into the milk inlet 3 and thus into the mixing area 4. The rinsing medium now flowing through the milk flow path will rinse and clean said milk flow path such that a contaminated rinsing medium/water mix will be drained from the outlet nozzle 5 of the mixing head 2.

In case the rinsing medium in the second receptacle 12 is water, this water can be supplied selectively from the downstream side of the pump 18 by means of a selectively operable valve 24 such as a solenoid valve. Preferably, a rinsing fluid line 51 is provided in fluid communication with the main water line after the pump and before heating block so that non-heated water can be delivered in the rinsing fluid receptacle 12. The valve 24 is thus installed between the main water line and rinsing fluid line 51 in order to selectively deliver water either to the heating block or to fill in the rinsing fluid receptacle 12. In other words, in such a scenario a portion of the water supplied by the pump 18 can be supplied to the second receptacle 12 to serve as a rinsing medium.

The contaminated rinsing medium leaving the outlet nozzle 5 of the mixing head 2 will accumulate in the combined receptacle 29. After having finished a controlled rinsing step in the position according to FIG. 8, the mixing head 2 can again be transferred into the intermediate position as shown in FIG. 6 in which the user can remove the combined receptacle 29 to dispose of the contaminated rinsing medium, to further clean the receptacle and then refill milk into the milk receptacle 13 and eventually even to refill a rinsing medium 6 into the second receptacle 12.

FIG. 9 shows a control unit which can be implemented e.g. as an ASIC or a microprocessor. The control unit 41 can carry out a pre-programmed processing triggered by a user's input command e.g. via the already mentioned button 42. E.g. upon manipulation of such control button 42 the control unit 41 can control cyclically the respectively subsequent one of the following states:

stand-by state according to FIG. 6
  operation state according to FIG. 7, and
  rinsing state according to FIG. 8.

To this effect the control unit 41 is supplied with input signals reflecting the current state of the device, such as e.g.

the presence of the receptacle 29 (detected by the contact switch 30), the current position of the mixing head 2 (via the contact switches 58, 59, 60 at the guiding curves 14, 14' activated by the cams),
  the position of the cup support (by means e.g. of the contact switch 57),
  the level of the upper rim 38 of the cup 23 (detected e.g. by an optical sensor), and
  the water steam temperature or pressure.

Depending on the user's input and the current value of the above input signals, the control unit can calculate and generate e.g., the following output signals activation of an actuator for the spindle 25,
  control of the actuator (electric motor) 27 for the belt drive 28,
  control of the heating block 19,
  control of the pump 18, and
  control of the valves 24 and 53.

What is claimed is:

1. A mixing head for producing heated milk comprising a steam feed which feeds steam to the mixing head, a milk inlet, a mixing area where the steam feed and milk inlet join and wherein the steam from the steam feed and the milk from the milk inlet combine to form a mixture, an outlet nozzle for draining the mixture from the mixing head, a rinsing medium supply, a milk supply, and a mechanism for bringing the milk inlet into fluid connection with either the rinsing medium supply or the milk supply, such that milk or a rinsing medium can enter the mixing head at the milk inlet, and when the rinsing medium enters the mixing head it cleans any residual milk from the milk inlet.

2. The mixing head according to claim 1, wherein the mechanism comprises a transfer member that provides relative movement between the milk inlet and the rinsing medium supply.

3. The mixing head according to claim 1, wherein the mechanism comprises a transfer member that provides relative movement between the milk inlet and the milk supply.

4. The mixing head according to claim 1, designed such that, when the milk inlet is in fluid connection with the rinsing medium supply, any fluid leaving the outlet nozzle is transferred into a milk supply receptacle such that any residual milk can be removed from the mixing head.

5. The mixing head according to claim 1, wherein the milk inlet is adapted to be selectively provided in sealing engagement with a milk supply receptacle that includes the milk supply.

6. A mixing head for producing heated milk comprising a steam feed which feeds steam to the mixing head, a milk inlet, a mixing area where the steam feed and milk inlet join and wherein the steam from the steam feed and the milk from the milk inlet combine and to form an emulsified mixture, an outlet nozzle for draining the mixture from the mixing head, a milk supply receptacle, and a mechanism for selectively bringing the outlet nozzle into a position in which any fluid leaving the outlet nozzle is transferred actively or passively into the milk supply receptacle such that any residual milk can be removed from the mixing head.

7. The mixing head according to claim 6, wherein the milk inlet is adapted to be selectively provided in sealing engagement with a milk supply receptacle that includes the milk supply.

8. The mixing head according to claim 6, further comprising a transfer member that provides relative movement between the mixing head and a rinsing medium supply receptacle.

9. The mixing head according to claim 6, further comprising a transfer member that provides relative movement between the mixing head and a milk supply receptacle.

10. A device for producing heated milk comprising a housing and a mixing head comprising a steam feed which feeds steam to the mixing head, a milk inlet, a mixing area where the steam feed and milk inlet join and wherein the steam from the steam feed and the milk from the milk inlet combine and to form a mixture, an outlet nozzle for draining the mixture from the mixing head, and a transfer mechanism for moving the outlet nozzle to either a retracted position where the mixing head outlet nozzle are configured and positioned to be cleaned or rinsed, or a product delivery position in which the outlet nozzle protrudes from a front wall of the housing to deliver the mixture.

11. The device according to claim 10, wherein, in the retracted position the mixing head becomes flush with the front wall of the housing.

12. The device according to claim 10, wherein the mixing head is displaceable in a rotational movement along at least one guiding curve between the retracted and product delivery positions.

13. The device according to claim 10, further comprising a water tank, a pump and a heating unit for producing the steam supplied to the steam inlet of the mixing head.

14. The device according to claim 13, wherein the rinsing medium supply receptacle can be selectively put in fluid connection with a circuit connecting a secondary side of the pump with the heating unit.

15. A beverage production machine comprising a device according to claim 10.

16. A beverage production machine comprising a housing and the mixing head according to claim 1.

17. A beverage production machine comprising a housing and the mixing head according to claim 6.

18. A method for cleaning or rinsing of a mixing head according to claim 1, which comprises bringing the milk inlet of the mixing head into fluid contact with a rinsing medium supply, and having a rinsing medium from the supply enter the milk inlet and pass through the mixing head to remove milk residues before leaving the mixing head at the outlet nozzle.

19. The method of claim 18, which further comprises entering the rinsing medium in the milk inlet by effect of the liquid suction created as a result of passing the steam into the mixing head.

20. The method of claim 18, which further comprises moving the milk inlet to connect to the rinsing medium supply to the mixing head.

21. The method of claim 20, wherein milk inlet is moved via a mechanical transfer mechanism.

22. The method of claim 21, wherein the mechanical transfer mechanism is motorized and is operatively associated with a control unit that controls the movement of the mechanical transfer mechanism.

\* \* \* \* \*